United States Patent [19]

Tsuchihashi et al.

[11] 4,237,298
[45] Dec. 2, 1980

[54] AROMATIC ACETIC ACID DERIVATIVES HAVING SULFUR ATOM AT ALPHA-POSITION AND PROCESS FOR THEIR PREPARATION

[75] Inventors: Genichi Tsuchihashi, Tama; Katsuyuki Ogura, Sagamihara, both of Japan

[73] Assignee: Sagami Chemical Research Center, Tokyo, Japan

[21] Appl. No.: 966,750

[22] Filed: Dec. 5, 1978

Related U.S. Application Data

[62] Division of Ser. No. 773,114, Feb. 28, 1977, Pat. No. 4,144,248.

[30] Foreign Application Priority Data

Mar. 4, 1976 [JP] Japan .................................. 51/22672
Mar. 4, 1976 [JP] Japan .................................. 51/22673
Dec. 27, 1976 [JP] Japan ................................. 51/156356

[51] Int. Cl.$^3$ .................. C07D 333/24; C07D 307/16; C07D 295/14; C07C 149/40
[52] U.S. Cl. ...................................... 546/238; 549/79; 260/347.2; 560/15
[58] Field of Search ..................... 260/332.2 A, 347.2; 560/15; 549/78, 79, 80; 424/275, 285; 546/238

[56] References Cited

U.S. PATENT DOCUMENTS 3,910,958  10/1975  Tsuchihashi et al. .......... 260/340.5 R

FOREIGN PATENT DOCUMENTS 1277578  6/1972  United Kingdom .

OTHER PUBLICATIONS

Gronowitz et al. "On the Reaction of 1-Methylsulfinyl-1-Methylthio-2-Arylethenes with Methanol and Hydrogen Chloride," Chemica Scripta, 1976, 10(2) 90-96. See Chemical Abstracts (1977) (vol. 86).
Tsuchihashi, Genichi et al., "Alpha-Haloarylacetic Acid Derivatives," Japan Kokai 75-19, 732m, Mar. 1, 1975, See Chemical Abstracts 83 (1975).
Tsuchihashi, Genichi et al., "Alpha-Chlorination of Sulfoxides by Chlorine," Bull. Chem. Soc. Jap. (1970) 43(7), p. 2271, See Chemical Abstracts 73 (1970).
Tsuchihashi, Genichi et al., "Alpha-Chlorination of Sulfoxides with N-Chlorosuccinimide," Bull. Chem. Soc. Jap. (1971) 44(6) p. 1726, see Chemical Abstracts 75 (1971).
Tsuchihashi, Genichi et al., "Chlorination of Sulfoxides with Sulfuryl Chloride," Synthesis (1971) vol. 2, pp. 89-91, see Chemical Abstracts 74 (1971).

*Primary Examiner*—Natalie Trousof
*Assistant Examiner*—L. Hendriksen
*Attorney, Agent, or Firm*—Wenderoth, Lind & Ponack

[57] ABSTRACT

Aromatic acetic acid derivatives having a sulfur atom at the alpha-position, and a process for their preparation. Useful drugs can be produced from derivatives. erivatives.

7 Claims, No Drawings

AROMATIC ACETIC ACID DERIVATIVES HAVING SULFUR ATOM AT ALPHA-POSITION AND PROCESS FOR THEIR PREPARATION

This is a division of application Ser. No. 773,114, filed Feb. 28, 1977, now U.S. Pat. No. 4,144,248.

This invention relates to a novel process for preparing aromatic acetic acid derivatives having a sulfur atom at the α-position, and novel aromatic acetic acid derivatives.

The compounds prepared by the process of this invention are acetic acid derivatives of the general formula

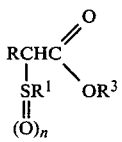
(III)

and are characterized by having a sulfur atom at the α-position. In formula (III), R represents an aryl, thienyl or furyl group, $R^1$ represents an alkyl group, $R^3$ represents a hydrogen atom or an alkyl group, and n is an integer of 0, 1 or 2. The groups R, $R^1$ and $R^3$ may be substituted by substituents which do not directly participate in the reaction. Specific examples of the aryl group represented by R are a phenyl group and phenyl groups substituted by halogen, alkyl, alkoxy, aryloxy, aroyl or amino. The amino-substituted phenyl group means a phenyl group substituted by primary, secondary or tertiary amino which is expressed by the following general formula

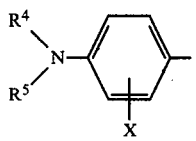

wherein $R^4$ and $R^5$ represent a hydrogen atom or an alkyl group containing 1 to 5 carbon atoms, or together represent an alkylene group, and X represents a hydrogen or halogen atom.

The compounds of formula (III) are useful as intermediates for the preparation of various organic compounds, especially medicines. Their utility will be briefly described below.

Compounds of formula (III) wherein R is a thienyl or furyl group are novel compounds, and can be converted to useful medicines. Compounds resulting from the condensation of these compounds with the amino group at the 7-position of 7-aminocephem derivatives have superior antibacterial spectra, and are especially effective as antibacterial agents against Gram-positive bacteria such as Staphylococcus epidermidis, Sarcina lutea and Coryne-bacterium diphtheriae, and Gram-negative bacteria such as Shigella flexineri, Proteus vulgaris and Escherichia coli (see Referential Example 2 to be given hereinbelow).

Compounds of formula (III) wherein R is a phenyl group have been known heretofore, and it is also known that these compounds are effective as chemical modifiers for penicilin and cephalosporins which are β-lactam type antibiotics (German OLS No. 1,933,629, and Japanese Laid-Open Pat. Nos. 49789/73 and 59386/75).

Compounds of formula (III) wherein R represents an alkyl-, benzoyl-, or phenoxy-substituted phenyl group are novel compounds, and can be converted to useful drugs. For example, α-(p-isobutylphenyl)propionic acid or its ester can be prepared easily by introducing a methyl group into the α-position of an acetic acid derivative of formula (III) in which R is an isobutylphenyl group, and reductively desulfurizing the resulting product (see Referential Example 3 to be given hereinbelow). This compound is called Ibuprofen and known to have antiinflammatory, analgesic and antipyretic actions.

Likewise, methylaction and reductive desulfurization of a compound of formula (III) in which R is a phenoxyphenyl group easily afford α-(m-phenoxyphenyl) propionic acid or its ester(see Referential Example 4 to be given hereinbelow). This product is called Fenoprofen, and possesses the same pharmacological actions as Ibuprofen.

A similar procedure can afford α-(m-benzoylphenyl) propionic acid or its ester which is known as Ketoprofen and has the same pharmacological actions as Ibuprofen.

Conventional methods for producing these pharmaceuticals are complicated and industrially disadvantageous. Since this fact has some bearing in demonstrating the advantages of the present invention, these known methods will be described below at some length.

Typical methods for producing Ibuprofen heretofore used are as follows:

(A) The method which comprises reacting a p-isobutylphenylacetic acid ester with a dialkyl carbonate in the presence of a base to produce the corresponding malonic acid ester, methylating the malonic acid ester with methyl iodide, hydrolyzing the methylated product, and subsequently pyrolyzing the hydrolyzate to obtain the desired propionic acid (British Pat. No. 971,700/64; and Japanese Pat. No. 7491/65).

(B) The method which comprises converting p-isobutylacetophenone to the corresponding hydantoin by the action of potassium cyanide and ammonium carbonate, hydrolyzing the hydantoin to form an α-amino acid, alkylating it to form dialkylamino compound, and then reducing it to form α-(p-isobutylphenyl)propionic acid (Japanese Pat. No. 18105/72).

(C) The method which comprises subjecting p-isobutylacetophenone and a monochloroacetic acid ester to the Darzen reaction to form the corresponding epoxycarboxylic acid ester, hydrolyzing the product, decarboxylating the hydrolyzate to form α-(p-isobutylphenyl)propionaldehyde, and oxidizing it to form the desired propionic acid (Japanese Pat. No. 24550/72).

All of these conventional methods start from p-isobutylacetophenone. p-Isobutylacetophenone can be prepared by a Friedel-Crafts reaction of isobutylbenzene with acetyl chloride. Since aluminum chloride is used in this reaction in an amount of more than 1 mole per mole of the starting compounds, a large quantity of aluminum hydroxide formed by a usual work-up in mass production causes serious troubles in isolating the desired product or in disposing of the waste matter.

Conventional methods for producing Fenoprofen are shown below.

(1) The method which comprises reducing m-phenoxy acetophenone with sodium borohydride to form m-phenoxy-α-phenethyl alcohol, reacting it with phosphorus tribromide to form m-phenoxy-α-phenethyl bromide, reacting the bromide with sodium cyanide in dimethyl sulfoxide under heat, and hydrolyzing the product with sodium hydroxide to form the desired α-(m-phenoxyphenyl)propionic acid (U.S. Pat. No. 3,600,437).

(2) The method which comprises brominating m-methyldiphenyl ether with N-bromosuccinimide to form m-(bromomethyl)diphenyl ether, reacting it with sodium cyanide in dimethylsulfoxide to form m-(cyanomethyl)diphenyl ether, hydrolyzing and esterifying it to form ethyl α-(m-phenoxyphenyl)acetate, reacting the resulting ester with diethyl carbonate in the presence of metallic sodium to form diethyl 2-(m-phenoxyphenyl)malonate, reacting the product with methyl iodide to form diethyl 2-methyl-2-(m-phenoxyphenyl)-malonate, hydrolyzing the product to form 2-methyl-2-(m-phenoxyphenyl)malonic acid, and decarboxylating the product under heat to form α-(m-phenoxyphenyl)propionic acid (Japanese Pat. No. 45586/76).

In method (1), m-phenoxyacetophenone is used as a starting material. This material is obtained by reacting m-hydroxyacetophenone, which is expensive and not easily available, with bromobenzene in the presence of copper. The intermediate, m-phenoxy-α-phenethyl bromide, is an unstable compound, and methods going through this intermediate are not suitable for mass production. In addition, it is essential in this method to use sodium cyanide which is an exceedingly poisonous substance. Method (2) involves a number of process steps including a step of using an expensive reagent such as N-bromosuccinimide and a step of using a poisonous substance such as sodium cyanide. Therefore, these two conventional methods are not industrially advantageous.

Compounds of formula (III) in which R represents an aminophenyl group are also novel compounds, and can be converted to useful medicines. For example, from a compound of formula (III) wherein R is a primary aminophenyl group, α-[p-(1-oxo-2-indolinyl)phenyl]propionic acid, termed Indoprofen [Arzneim.—Forsch. (Drug Res.), 23, 1090 (1973)] can be easily synthesized by reaction with phthalic anhydride, followed by methylation, hydrolysis and reduction (see Referential Example 5 to be given hereinbelow). Furthermore, α-[p-(pyryl-1)phenyl]propionic acid or α-[p-(pyryl-1)phenyl]butyric acid having anti-inflammatory and analgesic actions can be synthesized from it by reaction with 2,5-dimethoxytetrahydrofuran, followed by methylation or ethylation, hydrolysis, and reduction (U.S. Pat. No. 3,673,212).

A compound of formula (III) wherein $R^4$ and $R^5$ together form —$(CH_2)_5$— and the benzene ring is further substituted by chlorine can be similarly methylated, hydrolyzed and reductively desulfurized to afford α-[3-chloro-4-(piperidino-1)phenyl]propionic acid (U.S. Pat. No. 3,641,040).

Conventional methods for synthesizing α-phenylalkanecarboxylic acids having an N-substituent at the p-position are complicated and commercially disadvantageous. This will be described with regard to Indoprofen as an example.

Typical conventional methods for production of Indoprofen are as follows:

(A) The method which comprises reacting an aniline derivative of the general formula

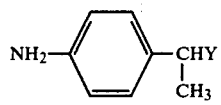

wherein Y represents a carboxyl, alkoxycarbonyl or cyano group,
with o-cyanobenzyl bromide, phthalide, thiophthalide or phthaldehyde, and then hydrolyzing the product with a base or acid (Japanese Pat. No. 11627/76).

(B) The method which comprises reacting the compound of formula (A) with phthalic anhydride, a phthalic acid diester or N-sulfonyl phthalimide to form a compound of the general formula

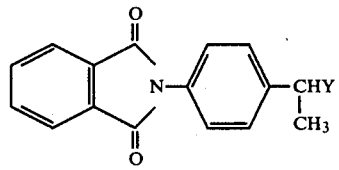

wherein Y is as defined above,
reducing the product to an isoindolinone compound using a suitable reducing agent, and if desired hydrolyzing the product (Japanese Pat. No. 11627/76, and Japanese Laid-Open Pat. No. 65755/76).

(C) The method which comprises reacting the compound of formula (A) with benzaldehyde, reducing the product, reacting the reduced product with phosgene to form a compound of the general formula

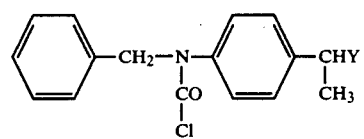

intramolecularly cyclizing the product by a Friedel-Crafts reaction, and if desired, hydrolyzing the product (Japanese Laid-Open Pat. No. 57965/73).

All of these conventional methods start from the compound of formula (A) which is synthesized from toluene through many steps. One suggested method for producing the compound of formula (A) comprises chlorinating toluene, converting the chlorinated product to benzyl cyanide by a substitution reaction using sodium cyanide, ethoxycarbonylating, methylating the α-position of this product, further subjecting the product to hydrolysis and decarboxylation to form α-phenylpropionitrile, nitrating this compound, solvolyzing the nitrile moiety, and reducing the nitro moiety [see G. Nannini et al., Arzneim.-Forsch. (Drug Res.), 23, 1090 (1973)].

Accordingly, these prior methods are extremely disadvantageous for industrial operation since they require a large number of process steps, and the use of sodium cyanide, an extremely poisonous substance, is essential.

The present invention provides a novel process for producing useful compounds of formula (III); and novel compounds falling within the definition of formula (III).

Compounds of formula (III) in which $R^3$ is hydrogen (i.e., compounds in acid form) can be easily derived by hydrolysis from compounds of formula (III) in which $R^3$ is alkyl (i.e., compounds in ester form). Furthermore, sulfinyl compounds of formula (III) in which n is 1, and sulfonyl compounds of formula (III) in which n is 2 can be easily obtained by oxidizing thio compounds of formula (III) in which n is 0. These three kinds of compounds have substantially the same utility. Accordingly, all of these compounds can be described and discussed as falling chemically within the genus of acetic acid derivatives having a sulfur atom at the α-position.

First of all, the production of α-(alkylthio)-acetic acid derivatives of formula (III) in which $R^3$ is an alkyl group and n is 0, that is, those expressed by the following formula

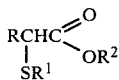 (IIIa)

wherein $R^2$ is an alkyl group, and R and $R^1$ are as defined above, will be described.

Previously, a method was suggested for producing compounds of formula (IIIa) in which R is phenyl. This method comprises reacting an α-haloester with an alkanethiol in the presence of a base. Since in this conventional method, a reductive dehalogenation reaction occurs mainly, the yield of the desired product is extremely low so that the method is not feasible for commercial production [M. Oki. W. Funakoshi, and A. Nakamura, Bull. Chem. Soc. Japan, 44, 828 (1971)]. Moreover, the α-haloesters used as a starting material are obtained by halogenation and esterification of the corresponding carboxylic acids many of which are generally difficult to obtain commercially.

According to the process of this invention to be described below in detail, such defects of the prior methods have been eliminated, and the final products can be easily obtained in good yields from commercially readily available materials.

The process of this invention for producing the α-(alkylthio)acetic acid esters of formula (IIIa) comprises reacting α-chloroketene mercaptals of the formula

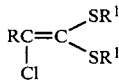 (II)

wherein R and $R^1$ are as defined above, with alcohols of the formula

wherein $R^2$ is as defined above,
in the presence of acid catalysts. Preferably, the alkyl group represented by $R^1$ and $R^2$ contains 1 to 5 carbon atoms. The α-chloroketene mercaptals of formula (II) and their production will be described hereinbelow.

The acids used as catalyst may be inorganic or organic acids. Preferred inorganic acids include sulfuric acid, perchloric acid, hydrogen, and hydrogen bromide. Preferred organic acids include p-toluenesulfonic acid, trifluoroacetic acid and trichloroacetic acid. Since the acids act as catalyst, their amount may be small (that is, a catalytic amount). The reaction can be performed in the presence of an inert solvent. Conveniently, the alcohol employed as a reactant can be utilized as a solvent when it is used in an excessive amount. Generally, the reaction proceeds smoothly at a temperature of 0° to 150° C., and gives the final product in good yields. It is preferred to perform the reaction at the refluxing temperature of the reaction system since it renders the operation simple. Isolation of the desired reaction product from the reaction mixture can be performed by conventional means such as chromatography, fractional distillation, or extraction.

The α-chloroketene mercaptal of formula (II) used as a reactant in this reaction has been found to be easily obtainable by reacting a ketene mercaptal S-oxide of the formula

 (I)

wherein R and $R^1$ are as defined above, with an acid chloride.

The ketene mercaptal S-oxides of formula (I) and a process for their production were invented before by the present inventors, and are disclosed in the following specifications:

U.S. Pat. No. 3,910,958 and U.S. patent application Ser. No. 651,112, now U.S. Pat. No. 4,051,151

Simply stated, the ketene mercaptan S-oxide of formula (I) can be easily produced by reacting an aldehyde of the formula RCHO with a formaldehyde mercaptal s-oxide of the formula $R^1SCH_2SOR^1$ in the presence of a base. Hence, it is a compound which can be produced from readily available, inexpensive materials with commercial advantage, and is easily available.

Suitable acid chlorides to be reacted with the ketene mercaptal S-oxides of formula (I) include thionyl chloride, phosphorus oxychloride, acetyl chloride, methanesulfonyl chloride, benzenesulfonyl chloride, p-toluenesulfonyl chloride, and phosgene. Of these thionyl chloride and phosphorus oxychloride are especially preferred since they cause the reaction to proceed smoothly and give high yields. The suitable amount of the acid chloride is almost equimolar to the compound of formula (I). Preferably, the reaction should be performed in an aprotic solvent such as methylene chloride, chloroform, tetrahydrofuran, diethyl ether, or benzene. The reaction proceeds smoothly at a temperature of −100° C. to room temperature, and in order to simplify the operation, temperatures of −80° C. to room temperatures are preferred. The reaction is carried out preferably in the presence of a base as an acid acceptor in order to capture hydrogen chloride formed. Preferred bases are organic bases such as diethylamine, dicyclohexylamine, pyridine, and triethylamine. The amount of the base is preferably one sufficient to neutralize the hydrogen chloride completely.

As mentioned hereinabove, the α-chloroketene mercaptal of formula (II) used as a raw material for producing the α-alkylthioacetic acid ester can be easily prepared from the ketene mercaptal S-oxide of formula (I). Accordingly, in order to produce the ester of formula (IIIa) from the compound of formula (I), the ketene mercaptal S-oxide of formula (I) is reacted with an acid chloride in a first step to produce the α-chloroketene mercaptal of formula (II), and the resulting α-chloroketene mercaptal is reacted with an alcohol of the formula $R^2CH$ in the presence of an acid catalyst in a second step. The α-chloroketene mercaptal obtained in the first step can be used in the second-step reaction after isolation, or the reaction mixture obtained in the first step can be directly used in the second step without complete isolation.

It is interesting to note that where R is a para-aminophenyl group, the ketene mercaptal S-oxide of formula (I) can be directly converted to the compound of formula (IIIa) without resorting to the two-step procedure described above. Specifically, reaction of the compound of formula (I) in which R is a para-aminophenyl group with an alcohol $R^2OH$ in the presence of hydrogen chloride affords the corresponding compound of formula (IIIa). In this reaction, the concentration of hydrogen chloride is one important factor, and should be adjusted to 0.4 M to 7 M, preferably 0.5 M to 4 M, in the reaction system. An aprotic solvent such as diethyl ether, chloroform or benzene may be used as a reaction solvent, and an excessive amount of the alcohol as a reactant can also be used as a solvent. The reaction temperature is preferably from room temperature to the refluxing temperature of the solvent in order to simplify the operation.

The reaction of converting the compound of formula (I) to the compound of formula (II), and the reaction of converting the compound of formula (II) to the compound of formula (IIIa), which are novel reactions, can be expressed by the following equations.

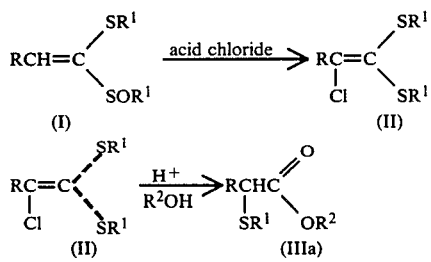

Now, the conversion of the α-(alkylthio)acetic acid ester of formula (IIIa) to the corresponding thioacetic acid, fulfinylacetic acid ester, sulfonylacetic acid ester, sulfinylacetic acid, and sulfonylacetic acid, which are expressed by the following formulae, will be described.

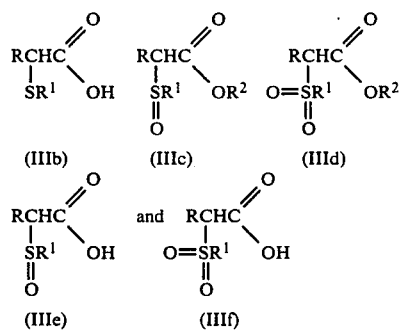

wherein R, $R^1$ and $R^2$ are as defind hereinabove.

As stated hereinabove, this conversion can be easily performed by customary chemical methods.

The compounds of formula (IIIb) can be obtained by hydrolyzing the compounds of formula (IIIa). The compounds of formulae (IIIc) and (IIId) can be obtained by oxidizing the compounds of formula (IIIa) with about 1 mole equivalent and 2 mole equivalents or more of oxidizing agents such as hydrogen peroxide or m-chloroperbenzoic acid. The compounds of formula (IIIe) and (IIIf) can be obtained by hydrolyzing and oxidizing the compounds of formula (IIIa) in an optional order, using an oxidizing agent in an amount of about 1 mole equivalent for producing the compound of formula (IIIe) and 2 mole equivalents or more for producing the compound of formula (IIIf) in the oxidation step. These compounds of formula (IIIa) to (IIIf) can be expressed by the following formula given at the outset of this specification.

As stated hereinabove, the present invention provides an industrially advantageous process for producing compounds of formula (III) which can be easily converted to useful medicines. Compounds of formula (III) other than those in which R is a phenyl group are novel, and the invention also provide such novel compounds. These novel acetic acid derivatives having a sulfur atom at the α-position can be expressed by the following formula

wherein R° represents thienyl, furyl, phenoxyphenyl, isobutylphenyl, benzoylphenyl, or the group of the formula

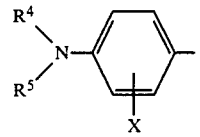

in which $R^4$ and $R^5$ represent a hydrogen atom or an alkyl group or together form an alkylene group, X is a hydrogen or halogen atom, $R^3$ represents a hydrogen atom or an alkyl group, and n is an integer of 0, 1 or 2.

The following Examples and Referential Examples specifically illustrate the present invention.

REFERENTIAL EXAMPLE 1

Some examples of the production of ketene mercaptal S-oxides of formula (I) are shown below.

(1) 2-Thiophene aldehyde (10.315 g) and 11.420 g of formaldehyde dimethyl mercaptal S-oxide (hereafter abbreviated as FAMSO) were dissolved in 50 ml of tetrahydrofuran, and 3 ml of a 40% methanol solution of trimethylbenzylammonium hydroxide was added. The mixture was heated under reflux for 6 hours. Methylene chloride (100 ml) was added, and the reaction mixture was washed with 3 N dilute sulfuric acid, followed by drying over anhydrous sodium sulfate. Distillation under reduced pressure afforded 17.31 g of 1-methylsulfinyl-1-methylthio-2-(thienyl-2)ethylene having a boiling point of 147° to 152° C./0.11–0.13 mmHg as a pale yellow oily substance. The yield was 86%.

Samples for analysis were obtained by re-distillation of this product. These samples had a boiling point of 151° C./0.11 mmHg.

IR (neat): 1055, 710 cm$^{-1}$

NMR (CDCl$_3$): δ2.35s(3H), 2.70s(3H), 7.05m(1H). 7.40m(2H), 7.86s(1H).

Elemental analysis for C$_8$H$_{10}$OS$_3$: Calculated: C,44.00; H,4.62; S,44.06. Found C,43.81; H,4.83; S,44.00.

(2) FAMSO (2.572 g), 3 ml of a 40% methanol solution of trimethylbenzylammonium hydroxide, and 3 ml of benzaldehyde were added to 5 ml of tetrahydrofuran, and the mixture was refluxed for 4 hours. After adding 100 ml of methylene chloride, the reaction mixture was washed with dilute sulfuric acid. The product was dried over anhydrous sodium sulfate, and concentrated under reduced pressure. The residue was chromatographed on a silica gel using methylene chloride as an eluant to afford 3.994 g of 1-methylsulfinyl-1-methylthio-2-phenylethylene as a colorless liquid having a boiling point of 149° to 150° C./0.08 mmHg in a yield of 91.0%.

IR (neat): 1062 cm$^{-1}$

NMR (CCl$_4$): δ2.62s(3H), 2.26s(3H), 7.51s(1H), 7.32m(3H), 7.85m(2H).

Mass spectrum (70 ev, 100° C.): m/e 212 (M$^+$, 7%), 197(5%), 149(100%), 134(96%), 116(18%), 115(14%), 89(11%).

Elemental analysis for C$_{10}$H$_{12}$OS$_2$: Calculated: C,56.65; H,5.72; S,30.33. Found: C,56.56; H,5.70; S,30.20.

(3) p-Isobutylbenzaldehyde (486 mg) and 450 mg of formaldehyde dimethyl mercaptal S-oxide were dissolved in 1 ml of t-butanol, and 2.0 ml of a 0.608 N t-butanol solution of potassium t-butoxide was added. The mixture was stirred at room temperature for 12 hours. Water (0.5 ml) and 50 ml of methylene chloride were added to the reaction mixture. The resulting mixture was dried over anhydrous sodium sulfate. The drying agent and the insoluble matter were removed by filtration, and the filtrate was concentrated under reduced pressure. The oily residue was chromatographed on a silica gel column using methylene chloride as an eluant to afford 701 mg of 1-methylsulfinyl-1-methylthio-2-(p-isobutylphenyl)ethylene in a yield of 87%. Samples for analysis were obtained by simple distillation of this product (at a bath temperature of 160° to 170° C./0.02 mmHg).

IR (neat): 1610, 1510, 1470, 1420, 1065, 950, 800 cm$^{-1}$

NMR (CDCl$_3$): δ0.91d(6H,J=6 Hz), 1.5–2.2m(1H), 2.33s(3H), 2.71d(2H,J=7 Hz), 2.76s(3H), 7.0–8.0 A$_2$B$_2$ q(4H), 7.59s(1H).

Elemental analysis for C$_{14}$H$_{20}$OS$_2$: Calculated: C,62.64; H,7.51; S,23.89. Found: C,62.32; H,7.48; S,24.07.

(4) FAMSC (1.27 g) and 2.00 g of m-phenoxybenzaldehyde were dissolved in 10 ml of tetrahydrofuran, and 1 ml of a 40% methanol solution of trimethylbenzylammonium hydroxide was added. The mixture was heated under reflux for 26 hours. Methylene chloride (50 ml) was added, and the reaction mixture was washed with 3 N dilute sulfuric acid. The product was dried over anhydrous potassium carbonate, concentrated under reduced pressure, and chromatographed on a silica gel column using methylene chloride as an eluant to afford 1.88 g of 1-methylsulfinyl-1-methylthio-2-(m-phenoxyphenyl)ethylene as a colorless oily substance.

IR (neat): 1062 cm$^{-1}$

NMR (CDCl$_3$): δ2.20s(3H), 2.66s(3H), 6.88–7.60m(9H), 7.52s(1H).

Mass spectrum (70 ev): m/e 304 (M$^+$, 5%), 242(19%), 241(base peak), 226(77%), 148(35%), 147(22%). 89(30%), 77(22%), 51(20%).

(5) Flakes of sodium hydroxide (55 mg) were added to a mixture of 201 mg of p-aminobenzaldehyde and 798 mg of FAMSO, and the mixture was stirred at 80° C. for 30 minutes. After adding 50 ml of a saturated aqueous solution of ammonium chloride, the reaction mixture was extracted with methylene chloride. The organic layer was dried over anhydrous sodium sulfate, and concentrated under reduced pressure. The residue was chromatographed on a silica gel column using methylene chloride as an eluant to afford oil-containing orange crystals. Washing of the crystals with acetone afforded 235 mg of 1-methylsulfinyl-1-methylthio-2-(p-aminophenyl)ethylene as pale yellow crystals in a yield of 62%. Samples for analysis were obtained as colorless crystals by recrystallization.

Melting point: 165.0°–165.5° C. (from acetone)

IR (nujol): 3440, 3320, 3200, 1170, 1010 cm$^{-1}$

Elemental analysis for C$_{10}$H$_{13}$NOS$_2$:

Calculated: C,52.83; H,5.76; N,6.16; S,28.20. Found: C,52.70; H,5.91; N,6.41; S,28.00.

(6) p-Dimethylaminobenzaldehyde (12.953 g) was dissolved in 30 ml of tetrahydrofuran, and 18.428 g of FAMSO and 12 ml of a 40% methanol solution of trimethylbenzylammonium hydroxide were added. The mixture was heated under reflux for 40 hours. Water was added, and the reaction mixture was acidified with acetic acid and then extracted with methylene chloride. The organic layer was washed with a saturated aqueous solution of sodium bicarbonate, dried over anhydrous sodium sulfate, and concentrated under reduced pressure. The residue was chromatographed on a silica gel column using methylene chloride/ethyl acetate as an eluant, and then recrystallized from diethyl ether to afford 13.492 g of 1-methylsulfinyl-1-methylthio-2-(p-dimethylaminophenyl)ethylene.

Melting point: 66.2°–66.8° C.

IR (nujol): 1045 cm$^{-1}$

NMR (CDCl$_3$): δ2.27s(3H), 2.66s(3H), 2.98s(6H), 7.46s(1H), 6.66d(2H,J=9 Hz), 7.86d(2H,J=9 Hz).

Elemental analysis for C$_{12}$H$_{17}$NOS$_2$: Calculated: C,56.44; H,6.71; N,5.48; S,25.10. Found: C,56.40; H,6.64; N,5.40; S,24.85.

(7) A 40% methanol solution of trimethylbenzyl ammonium hydroxide was added to a mixture of 3.011 g of 3-chloro-4-(piperidinyl-1)benzaldehyde and 6 ml of FAMSO, and the mixture was stirred at room temperature for 16 hours. Water was added, and the reaction mixture was extracted with methylene chloride. The organic layer was washed with a saturated aqueous solution of sodium bicarbonate, dried over anhydrous sodium sulfate, and concentrated under reduced pressure to afford 4.039 g of 1-methylsulfinyl-1-methylthio-2-[3-chloro-4-(piperidinyl-1)phenyl]ethylene as an oily substance in a yield of 91%.

IR (neat): 1063 cm$^{-1}$

NMR (CDCl$_3$): δ1.45–1.85m(6H), 2.29s(3H), 2.69s(3H), 2.9–3.1m(4H), 6.97d(1H,J=9 Hz), 7.67 dxd (1H,J=2 and 9 Hz), 7.99d(1H,J=2 Hz), 7.44s(1H).

Mass spectrum: m/e 331, 330, 329 (M$^+$), 266, 265, 251.

(8) m-Benzoylbenzaldehyde (902 mg) was added to 1 ml of FAMSO, and 60 mg of sodium hyroxide was added. The mixture was stirred at 95° C. for 70 minutes in an atmosphere of argon. Water (20 ml) was added, and the reaction mixture was extracted with methylene chloride. The organic layer was dried over anhydrous sodium sulfate, concentrated under reduced pressure, and chromatographed on a silica gel column using methylene chloride as an eluant to afford 1.035 g of 1-methylsulfinyl-1-methylthio-2-(m-benzoylphenyl)ethylene.

IR (nest): 1657, 1320, 1290, 1065, 723, 711 cm$^{-1}$

NMR (CDCl$_3$): δ2.30s(3), 2.76s(3H), 7.3–8.2m(9H), 8.26s(1H).

EXAMPLE 1

1-Methylsulfinyl-1-methylthio-2-(thienyl)-2)-ethylene (7.165 g) was dissolved in 25 ml of methylene chloride, and with stirring under ice cooling, a solution composed of 3 ml of thionyl chloride and 25 ml of methylene chloride was added dropwise over the course of 1 hour. The mixture was stirred at room temperature for 3 hours, and then 30 ml of water was added. The reaction mixture was then extracted with methylene chloride. The organic layer was separated, dried over anhydrous potassium carbonate, and concentrated under reduced pressure. The residue was chromatographed on a silica gel column using benzene as an eluant. The eluates were combined, and concentrated under reduced pressure. The residue was distilled under reduced pressure to afford 1.784 g of 1,1-bis(methylthio)-2-chloro-2-(thienyl-2)ethylene having a boiling point of 106° to 115° C./0.06–0.07 mmHg.

IR (neat): 2905, 1418, 1228, 797, 701 cm$^{-1}$

NMR (CDCl$_3$): δ2.16s(3H), 2.42s(3H), 6.91 d×d(1H, J=4 and 5 Hz), 7.23 d×d(1H, J=1 and 5 Hz), 7.43 d×d(1H, J=1 and 4 Hz).

EXAMPLE 2

1-Methylsulfinyl-1-methylthio-2-(thienyl-2)-ethylene (5.052 g) was dissolved in 25 ml of methylene chloride, and 4 ml of triethylamine was added. Then, a solution of thionyl chloride (2 ml) in 25 ml of methylene chloride was added dropwise at −10° C. The mixture was stirred at −10° C. for 35 minutes. Water (30 ml) was added, and the reaction mixture was extracted with 100 ml of methylene chloride. The organic layer was separated. The water layer was extracted twice with 50 ml of methylene chloride. The organic layers were combined, dried over anhydrous potassium carbonate, and concentrated under reduced pressure. The residue was chromatographed on a silica gel column using benzene as an eluant. The eluates were collected, and distilled under reduced pressure to afford 3.869 g of a fraction having a boiling point of 113° to 124° C./0.063–0.1 mmHg.

The product was dissolved in 50 ml of methanol, and 0.5 ml of methanol saturated with hydrogen chloride was added. The mixture was then heated under reflux for 8 hours, and concentrated under reduced pressure. Distillation of the residue under reduced pressure afforded 2.322 g of methyl α-methylthio(thienyl)-2)acetate as a pale yellow oil.

Boiling point: 97°–100° C./0.08 mmHg

IR (neat): 1740, 1433, 1313, 1243, 1150, 703 cm$^{-1}$

NMR (CDCl$_3$): δ2.13s(3H), 3.80s(3H), 4.80s(1H), 6.8–7.35m(3H).

Elemental analysis for C$_8$H$_{10}$O$_2$S$_2$: Calculated: C,47.50; H,4.98; S,31.70. Found: C,47.84; H,5.10; S,31.33.

EXAMPLE 3

1-Methylsulfinyl-1-methylthio-2-(thienyl-2)-ethylene (1.523 g) was dissolved in 5 ml of methylene chloride, and 1 ml of triethylamine was added. With stirring under ice cooling, a solution consisting of 0.6 ml of thionyl chloride and 5 ml of methylene chloride was added dropwise. The mixture was stirred at room temperature for 1 hour. Methylene chloride (100 ml) and water were added. The resulting organic layer was separated. The aqueous layer was extracted twice with 30 ml of methylene chloride. The organic layers were combined, dried over anhydrous sodium sulfate, and concentrated under reduced pressure. The residue was chromatographed on a column of Florisil (i.e., chromatographic magnesium silicate) using benzene/n-hexane as an eluant to afford 1.394 g of a yellow oil. From its NMR spectrum, this product was found to be a mixture of 1,1-bis(methylthio)-2-chloro-2-(thienyl-2)ethylene and 1,1-bis(methylthio)-2-(thienyl-2)ethylene, and contain 1.214 g of the desired 1,1-bis(methylthio)-2-chloro-2-(thienyl-2)ethylene. The yield was 73.5%.

EXAMPLE 4

The crude product obtained in Example 3 (325 mg) was dissolved in 10 ml of methanol, and 0.1 ml of methanol saturated with hydrogen chloride was added. The mixture was heated under reflux for 5 hours. The reaction mixture was concentrated under reduced pressure, and chromatographed on a silica gel column using benzene/n-hexane as an eluant to afford 258 mg of a colorless oil.

From its NMR spectrum, this product was determined to be a mixture consisting of 236 mg of methyl α-methylthio(thienyl-2)acetate and 22 mg of methyl 2-thienylacetate.

EXAMPLE 5

The mixture (204 mg) of methyl α-methylthio (thienyl-2)acetate and methyl 2-thienylacetate obtained in Example 4 was dissolved in 10 ml of methanol, and 0.4 ml of a 30% aqueous solution of hydrogen peroxide and 15 mg of sodium tungstate dihydrate were added. The mixture was stirred at room temperature for 3 days. Water (40 ml) was added, and the reaction mixture was extracted thrice with 40 ml of methylene chloride. The organic layer was dried over anhydrous sodium sulfate, concentrated under reduced pressure, and chromatographed on a silica gel column using benzene/methylene chloride as an eluant to afford 196 mg of methyl α-methylsulfonyl(thienyl-2)acetate as colorless crystals.

Melting point: 102.5°–103.5° C. (from benzene/hexane)

IR (KBr): 1738, 1339, 1320, 1302, 1220, 1117 cm$^{-1}$

NMR (CDCl$_3$): δ2.95s(3H), 3.90s(3H), 5.22s(1H), 6.9–7.5m(3H).

Elemental analysis for C$_8$H$_{10}$O$_4$S$_2$: Calculated: C,41.01; H,4.30; S,27.37. Found: C,40,90; H,4.23; S,27.09.

EXAMPLE 6

Methyl α-methylthio(thienyl-2)acetate (1.956 g) was dissolved in 20 ml of 1,2-dimethoxyethane, and 10 ml of a 2 N aqueous solution of potassium hydroxide was added. The mixture was stirred at room temperature for 2 hours and 50 minutes. Water (20 ml) and 10 ml of 3 N sulfuric acid was added. The mixture was then extracted four times with 50 ml of diethyl ether. The ethereal layers were combined, dried with anhydrous sodium sulfate, and concentrated under reduced pressure to afford 1.668 g of α-methylthio(thienyl-2)acetic acid as pale yellow crystals. The crystals were purified by recrystallization from diethyl ether/n-hexane.

Melting point: 75°–75.5° C.

IR (neat): 3200–2300, 1700 cm$^{-1}$

NMR (CDCl$_3$): δ2.15s(3H), 4.76s(1H), 6.86–7.32m(3H), 9.59 broad s (1H).

Elemental analysis for C$_7$H$_8$O$_2$S$_2$: Calculated: C,44.66; H,4.28; S,34.06. Found: C,44,53; H,4.22; S,34.05.

EXAMPLE 7

α-Methylthio(thienyl-2)acetic acid (1.731 g) and 10 mg of sodium tungstate were added to 20 ml of methanol, and 3.34 ml of a 30% aqueous solution of hydrogen peroxide was added. The mixture was stirred at room temperature for 70 hours. Water (30 ml) and 30 ml of methylene chloride were added. The resulting organic layer was separated. The aqueous layer was extracted four times with 30 ml of methylene chloride. The organic layers were combined, dried over anhydrous sodium sulfate, and concentrated under reduced pressure to afford yellow crystals. The crystals were dissolved in benzene, and the insoluble matter was separated by filtration. The filtrate was concentrated under reduced pressure. Recrystallization of the resulting yellow crystals from benzene hexane afforded 997 mg of α-methylsulfonyl(thienyl-2)acetic acid as pale yellow crystals.

Melting point: 126.5°–127° C.

IR (Kbr): 3600–2000, 1725 (sh), 1695, 1315, 1123 cm$^{-1}$

NMR (d$_6$-DMSO): δ2.98s(3H), 5.87s(1H), 7.05 d×d(1H, (1H, J=3.5 and 5 Hz), 7.26 d×d(1H, J=1 and 3.5 Hz), 7.60 d×d (1H, J=1 and 5 Hz).

Elemental analysis for C$_7$H$_8$O$_4$S$_2$: Calculated: C,38.17; H,3.66; S,29.12. Found: C,37.99; H,3.63; S,29.18.

EXAMPLE 8

Methyl α-methylthio(thienyl-2)acetate (1.067 g) and 10 mg of sodium tungstate were added to 20 ml of methanol, and 0.6 ml of a 30% aqueous solution of hydrogen peroxide was added. The mixture was stirred at room temperature for 35 minutes. Methylene chloride (50 ml) and 50 ml of water were added. The resulting organic layer was separated, and the aqueous layer was extracted three times with 50 ml of methylene chloride. The organic layers were combined, dried over anhydrous sodium sulfate, concentrated under reduced pressure, and chromatographed on a silica gel column using benzene as an eluant to afford 427 mg of a yellow oily substance. From its NMR and IR spectra, this product was determined to be a mixture of diastereoisomers of methyl α-methylsulfinyl(thienyl-2)acetate.

NMR (CDCl$_3$): δ
  Component A: 2.36s(3H), 3.60s(3H), 4.93s(1H). 6.97–7.40m(3H).
  Component B: 2.47s(3H), 3.60s(3H), 4.97s(1H), 6.97–2.40m(3H).

IR (neat): 1735, 1432, 1316, 1246, 1159, 1056, 708, 490 cm$^{-1}$

EXAMPLE 9

An 85:15 mixture (257 mg) of 1,1-bis(methylthio)-2-chloro-2-(thienyl-2)ethylene and 1,1-bis(methylthio)-2-(thienyl-2)ethylene was added to 15 ml of ethanol, and 0.1 ml of ethanol saturated with hydrogen chloride was added. The mixture was refluxed for 15 hours. The reaction mixture was concentrated under reduced pressure, and chromatographed on a silica gel column using benzene/hexane as an eluant to afford 214 mg of ethyl α-methylthio(thienyl-2)acetate as a colorless oil.

IR (neat): 1730 cm$^{-1}$

NMR (CDCl$_3$): δ1.28g(3H, J=7 Hz), 2.13s(3H), 4.22q (2H, J=7 Hz), 4.75s(1H), 6.8–7.4m(3H).

EXAMPLE 10

A 85:15 (mixture (1.902 g) of 1,1-bis(methylthio)-2-chloro-2-(thienyl-2)ethylene and 1,1-bis(methylthio)-2-(thienyl-2)ethylene was dissolved in 15 ml of n-butanol, and a drop of conc. sulfuric acid was added. The mixture was stirred at 65° C. for 31 hours. The reaction mixture was concentrated under reduced pressure, and chromatographed on a silica gel column using h-hexane/benzene as an eluant to afford 1.376 g of n-butyl α-methylthio(thienyl-2)acetate as a pale yellow oil.

IR (neat): 1737 cm$^{-1}$

NMR (CdCl$_3$): δ0.90t(3H,J=7 Hz), 1.17–1.79m(4H), 2.09s(3H), 4.14t(2H,J=6 Hz), 4.73s(1H), 6.83–6.96m(1H), 7.01–7.32 m(2H).

EXAMPLE 11

1-Isopropylsulfinyl-1-isopropylthio-2-(thienyl-2)ethylene (2.008 g) was dissolved in 20 ml of methylene chloride, and 1 ml of triethylamine was added. With stirring at −20° C., 0.6 ml of thionyl chloride was added dropwise. The mixture was stirred at −20° C. for 65 minutes, and 30 ml of water was added. The reaction mixture was then extracted three times with 30 ml of methylene chloride. The organic layer was dried over anhydrous potassium carbonate, and concentrated under reduced pressure. The residue was chromatographed on a silica gel column using hexane/benzene as an eluant to afford 2.025 g of yellow oil composed mainly of 1,1-bis(isopropylthio)-2-chloro-2-(thienyl-2)-ethylene.

IR (neat): 1230, 1152, 1050, 798, 702 cm$^{-1}$

NMR (CDCl$_3$): δ1.27d(6H,J=7 Hz), 1.32d(6H,J=7 Hz), 3.38 septet(1H,J=7 Hz), 3.55 septet(1H, J=7Hz), 6.83–6.98m(1H), 7.16–7.31m(1H), 7.42–7.56m(1H).

EXAMPLE 12

The yellow oil (939 mg) obtained in Example 11 was dissolved in 10 ml of methanol, and 0.1 ml of methanol saturated with hydrogen chloride was added. The mixture was refluxed for 26 hours and 50 minutes. The reaction mixture was concentrated under reduced pressure, and chromatographed on a silica gel column using hexane/benzene as an eluant to afford 181 mg of methyl α-isopropylthio(thienyl-2)acetate and 698 mg of 1,1-bis-(isopropylthio)2-chloro-2-(thienyl-2)ethylene. The results of analysis of the acetate were as follows:

IR (neat): 1743, 1401, 1243, 1140, 695 cm$^{-1}$

NMR (CDCl$_3$): δ1.14d(3H,J=7 Hz), 1.16d(3H,J=7 Hz), 2.94 septet (1H,J=7 Hz), 3.71s(3H), 4.86s(1H), 6.87 dxd(1H, J=4 and 5.5 Hz), 7.05 diffused d(1H, J=4 Hz), 7.10 diffused d(1H, J=5.5 Hz).

EXAMPLE 13

1,1-Bis(isopropylthio)-2-chloro-2-(thienyl-2)-ethylene (1.934 g) was dissolved in 30 ml of methanol, and 0.1 ml of 70% perchloric acid was added. The mixture was refluxed for 10 days. Water (30 ml) was added, and the reaction mixture was extracted three times with 40 ml of diethyl ether. The organic layer was dried over anhydrous sodium sulfate, and concentrated under reduced pressure. The residue was chromatographed on a silica gel column using n-hexane/benzene as an eluant to afford 555 mg of methyl α-isopropylthio(thienyl-2)acetate and 1153 mg of the unreacted starting material.

EXAMPLE 14

1-Methylsulfinyl-1-methylthio-2-(thienyl-3)-ethylene (11.734 g) was dissolved in 50 ml of methylene chloride, and 8 ml of triethylamine was added. With stirring at −50° C., a solution consisting of 4 ml of thionyl chloride and 25 ml of methylene chloride was added. The mixture was stirred at −15° C. to 0° C. for 2 hours. Water (50 ml) was added, and the reaction mixture was extracted four times with 50 ml of methylene chloride. The organic layer was dried over anhydrous potassium carbonate/anhydrous sodium sulfate, and concentrated under reduced pressure. The residue was chromatographed on an Florisil column using benzene as an eluant to afford 11.595 g of 1,1-bis(methylthio)-2-chloro-2-(thienyl-3)ethylene.

IR (neat): 828, 759 cm$^{-1}$
NMR (CDCl$_3$): δ2.17s(3H), 2.40s(3H), 7.06-7.34m(2H), 7.38-7.51m(1H).

EXAMPLE 15

1,1-Bis(methylthio)-2-chloro-2-(thienyl-3)ethylene (10.885 g) was dissolved in 100 ml of methanol, and 1 ml of methanol saturated with hydrogen chloride was added. The mixture was refluxed for 16 hours and 40 minutes. The reaction mixture was concentrated under reduced pressure. The residue was distilled under reduced pressure to afford 7.178 g of a fraction hving a boiling point of 80° to 95° C. (mainly 93° to 95° C.)/0.12 mmHg. From the following data, this product was determined to be methyl α-methylthio (thienyl-3)acetate. Samples for analysis were obtained by redistilling this product.

IR (neat): 1738 cm$^{-1}$
NMR (CDCl$_3$): δ2.04s(3H), 3.72s(3H), 4.56s(1H), 7.05-7.40m(3H).
Element analysis for C$_8$H$_{10}$O$_2$S$_2$: Calculated: C,47.50; H,4.98; S,31.70. Found: C,47.60; H,4.95; S,31.46.

EXAMPLE 16

Methyl α-methylthio(thienyl-3)acetate (5.045 g) was dissolved in 60 ml of 1,2-dimethoxyethane, and 20 ml of a 2 N aqueous solution of potassium hydroxide was added. The mixture was stirred at room temperature for 3 hours and 10 minutes. Water (30 ml) and 6 ml of 3 N dilute sulfuric acid were added. The reaction mixture was then extracted three times with 50 ml of diethyl ether. The organic layer was dried over anhydrous sodium sulfate, and concentrated under reduced pressure. The residue was recrystallized from benzene/hexane to afford 3.291 g of α-methylthio(thienyl-3)acetic acid as pale yellow crystals.

Melting point: 73.5°-74.0° C.
IR (KBr): 3400-2000, 1695, 1413, 1293, 1242, 1211, 1170 cm$^{-1}$.
NMR (CDCl$_3$): δ2.10s(3H), 4.56s(1H), 7.06-7.39m(3H), 9.86 broad(1H).
Elemental analysis for C$_7$H$_8$O$_2$S$_2$: Calculated: C,44.66; H,4.28; S,34.06. Found: C,44.84; H,4.30; S,33.80.

EXAMPLE 17

α-Methylthio(thienyl-3)acetic acid (1.487 g) was dissolved in 20 ml of methanol, and 10 mg of sodium tungstate and 2.5 ml of a 30% aqueous solution of hydrogen peroxide were added. The mixture was stirred for 3 days. Water (50 ml) was added, and the reaction mixture was extracted four times with 80 ml of methylene chloride. The organic layer was dried over anhydrous sodium sulfate, and concentrated under reduced pressure. Crystallization from methylene chloride/carbon tetrachloride afforded 950 mg of α-methylsulfonyl(thienyl-3)acetic acid as pale yellow crystals.

Melting point: 123°-123.5° C.
IR (KBr): 3600-2100, 1720 (sh), 1696, 1308, 1125 cm$^{-1}$
NMR (d$_6$-DMSO): δ3.30s(3H), 5.97s(1H), 7.59 dxd(1H, J=2 and 5 Hz), 7.93 dxd (1H, J=3 and 5 Hz), 8.06 dxd(1H, J=2 and 3 Hz).
Elemental analysis for C$_7$H$_8$O$_4$S$_2$: Calculated: C,38.17; H,3.66; S,29.12. Found: C,38.12; H,3.64; S,29.15.

EXAMPLE 18

1-Methylsulfinyl-1-methylthio-2-(furyl-2)ethylene (10.201 g) was dissolved in 50 ml of methylene chloride, and 8 ml of triethylamine was added. With stirring at −10° C., 4.4 ml of thionyl chloride and 25 ml of methylene chloride were added dropwise. The mixture was stirred at −10° to 0° C. for 1.5 hours, and then at 0° C. to room temperature for 2 hours. Water (50 ml) was added, and the reaction mixture was extracted four times with 50 ml of methylene chloride. The organic layer was dried over anhydrous sodium sulfate, and concentrated under reduced pressure. The residue was chromatographed on a Florisil column using hexane/benzene as an eluant to afford 5.670 g of a yellow oil consisting mainly of 1,1-bis(methylthio)-2-chloro-2-(furyl-2)ethylene.

The oil obtained was dissolved in 100 ml of methanol, and 1 ml of methanol saturated with hydrogen chloride was added. The mixture was refluxed for 15 hours and 10 minutes. The reaction mixture was concentrated under reduced pressure, and chromatographed on a silica gel column using hexane/benzene as an eluant to afford a pale yellow oil consisting mainly of 3.811 g of methyl α-methylthio(furyl-2)acetate.

IR (neat): 1744 cm$^{-1}$
NMR (CDCl$_3$): δ2.08s(3H), 3.73s(3H), 4.56s(1H), 6.29 dxd(1H, J=2 and 3 Hz), 6.41 dxd (1H, J=0.5 and 3 Hz), 7.34 dxd (1H, J=0.5 and 2 Hz).

The resulting oil was hydrolyzed in a customary manner at room temperature using potassium hydroxide in 1,2-dimethoxyethane. Crystallization of the resulting crude product from hexane/benzene afforded α-methylthio(furyl-2)acetic acid.

Melting point: 62.0-62.5° C.
IR (KBr): 3300-2000, 1698 cm$^{-1}$
NMR (CDCl$_3$): δ2.12s(3H), 4.58s(1H), 6.29 dxd (1H, J=2 and 3 Hz), 6.44 dxd (1H, J=1 and 3 Hz), 7.35 dxd (1H, J=1 and 2 Hz), 9.50 broad (1H).
Elemental analysis for C$_7$H$_8$O$_3$S: Calculated: C,48.82; H,4.68; S,18.62. Found: C,48.87; H,4.72; S,18.75.

EXAMPLE 19

α-Methylthio(furyl-2)acetic acid (659 mg) was dissolved in 10 ml of methanol, and 10 mg of sodium tungstate and 1.5 ml of a 35% aqueous solution of hydrogen peroxide were added. The reaction mixture was stirred at room temperature for 75 hours. Water (30 ml) was added, and the reaction mixture was extracted three times with 50 ml of methylene chloride. The organic layer was dried over anhydrous sodium sulfate, and concentrated under reduced pressure. The residual oil soon crystallized. The remaining oily substance was caused to be absorbed by an unglazed porcelain plate to afford 331 mg of α-methylsulfonyl(furyl-2)acetic acid as crystals.

Melting point: 97.0–97.5° C. (from chloroform/benzene)

IR (KBr): 3600–2200, 1725(sh), 1707, 1315, 1133 cm$^{-1}$

NMR (CDCl$_3$): δ3.04s(3H), 5.19s(1H), 6.46 dxd (1H, J=2 and 4 Hz), 6.75 dxd(1H, J=1 and 4 Hz), 5.51 dxd(1H, J=1 and 2 Hz), 8.92s(1H).

Elemental analysis for C$_7$H$_8$O$_5$S: Calculated: C,41.17; H,3.95; S,15.70. Found: C,44.11; H,3.82; S,15.58.

EXAMPLE 20

1-Methylsulfinyl-1-methylthio-2-phenylethylene (1.868 g) was dissolved in 10 ml of methylene chloride, and with stirring under ice cooling, a solution consisting of 0.71 ml of thionyl chloride and 6 ml of methylene chloride was added dropwise over the course of 30 minutes. Under ice cooling, the mixture was stirred for 1.5 hours, and concentrated under reduced pressure. The residue was chromatographed on a Florisil column using benzene/hexane as an eluant to afford 1.494 g of 1,1-bis(methylthio)-2-chloro-2-phenylethylene as a colorless oil.

IR (neat): 2910, 1440, 850, 735, 690 cm$^{-1}$

NMR (CDCl$_3$): δ2.17s(3H), 2.47s(3H), 7.38s(5H).

Mass spectrum: m/3 232 (M$^+$ +2, 42%), 230 (M$^+$, 99%), 180 (37%), 170(37%), 168(base peak), 133 (34%), 89(46%).

Oxidation of this compound with hydrogen peroxide in the presence of sodium tungstate afforded 1-methylsulfinyl-1-methylsulfonyl-2-chloro-2-phenylethylene.

Melting point: 143°–144° C. (from benzene/hexane)

IR (KBr): 1535, 1318, 1312 (sh), 1132, 1058, 980, 960, 743, 699, 540, 520 cm$^{-1}$

NMR (CDCl$_3$): δ3.24s(3H), 3.39s(3H), 7.2–7.6m(5H).

Elemental analysis for C$_{10}$H$_{11}$ClO$_3$S$_2$: Calculated: C,43.08; H,3.98; S,23.01. Found: C,43.41; H,3.92; S,23.05.

EXAMPLE 21

1,1-Bis(methylthio)-2-chloro-2-phenylethylene (601 mg) was added to 10 ml of methanol, and 0.1 ml of methanol saturated with hydrogen chloride was added. The mixture was refluxed for 5 hours, and concentrated under reduced pressure. The residue was chromatographed on a silica gel column using hexane/benzene as an eluant to afford 420 mg of methyl α-(methylthio)phenylacetate in a yield of 82%.

IR (neat): 1743 cm$^{-1}$

NMR (CDCl$_3$): δ2.03s(3H), 3.71s(3H), 4.50s(1H), 7.15–7.50m(5H).

Oxidation of this product with hydrogen peroxide in the presence of sodium tungstate in methanol gave a sulfone derivative.

Melting point: 104°–105° C. (from carbon tetrachloride/hexane)

IR (KBr): 1738, 1312, 1306 (sh), 1029 cm$^{-1}$

NMR (CDCl$_3$): δ2.92s(3H), 3.86s(3H), 4.99s(1H), 7.2–7.7m(5H).

Elemental analysis for C$_{10}$H$_{12}$O$_4$S: Calculated: C,52.62; H,5.30; S,14.05. Found: C,52.59; H,5.27; S,14.01.

EXAMPLE 22

1-Methylsulfinyl-1-methylthio-2-phenylethylene (1.154 g) was dissolved in 15 ml of methylene chloride, and 1 ml of triethylamine was added. Under cooling at −15° C., 0.55 ml of phosphorus oxychloride was added. The mixture was stirred at −15° C. for 1 hour and then at room temperature for 2 hours. Water (30 ml) was added, and the reaction mixture was extracted three times with 30 ml of methylene chloride. The organic layer was dried over anhydrous sodium sulfate, and concentrated under reduced pressure. The residue was chromatographed on a Florisil column using hexane/benzene as an eluant to afford 1.180 g of 1,1-bis(methylthio)-2-chloro-2-phenylethylene in a yield of 94%.

EXAMPLE 23

1-Methylsulfinyl-1-methyltyio-2-(p-isobutylphenyl)ethylene (701 mg) was dissolved in 2 ml of chloroform, and 0.50 ml of triethylamine was added. With stirring under ice cooling, 5 ml of a chloroform solution of 380 mg of thionyl chloride was added during 10 minutes. The mixture was further stirred for 30 minutes under ice cooling, and chloroform was added in an amount sufficient to adjust the total amount of the mixture to 30 ml. The mixture was then washed twice with 10 ml of water. The organic layer was dried over anhydrous sodium sulfate, concentrated under reduced pressure, and chromatographed on a Florisil column using benzene as an eluant to afford 628 mg of 1,1-bis(methylthio)-2-chloro-2-(p-isobutylphenyl) ethylene as a colorless oil in a yield of 84%.

IR (neat): 1505, 1470, 860, 850, 820, 795 760, 745 cm$^{-1}$

NMR (CDCl$_3$): δ0.89d(6H, J=6 Hz), 1.6–2.0m(1H), 2.12s(3H), 2.41s(3H), 2.44d(2H, J=7 Hz), 6.97–7.36 A$_2$B$_2$ q (4H).

Mass spectrum: m/e 288 (M$^+$ +2), 286 (base peak, M$^+$), 245, 243, 57.

EXAMPLE 24

1,1-Bis(methylthio)-2-chloro-2-(p-isobutylphenyl)ethylene (592 mg) was dissolved in 6 ml of anhydrous methanol, and 0.1 ml of methanol saturated with hydrogen chloride was added. The mixture was heated under reflux for 5 hours, concentrated under reduced pressure, and chromatographed on a silica gel column using benzene as an eluant to afford 471 mg of methyl α-methylthio(p-isobutylphenyl)acetate as a colorless oil in a yield of 90%.

IR (neat): 1745, 1150, 1010 cm$^{-1}$

NMR (CDCl$_3$): δ0.89d(6H, J=6 Hz), 1.5–2.1m(1H), 2.06s(3H), 2.43d(2H, J=7 Hz), 3.73s(3H), 4.47s(1H), 7.0–7.5 A$_2$B$_2$q(4H).

Mass spectrum: m/e 252 (M$^+$), 205, 193 (base peak).

EXAMPLE 25

1-Methylsulfinyl-1-methylthio-2-(m-phenoxyphenyl)ethylene (4.56 g) was dissolved in 40 ml of methylene chloride, and 2 ml of pyridine was added. With stirring under ice cooling, 10 ml of a methylene chloride solution of 2.15 g of thionyl chloride was added dropwise over the course of 5 minutes. The mixture was further stirred for 1 hour under ice cooling, and methylene chloride was added in an amount sufficient to adjust the total amount of the mixture to 80 ml. The mixture was then washed three times with 20 ml of water. The product was dried over anhydrous sodium sulfate, and concentrated under reduced pressure. The residue was chromatographed on a Florisil column using hexane/benzene as an eluant to afford 3.403 g of 1,1-bis(methylthio)-2-chloro-2-(m-phenoxyphenyl)-ethylene as an oil in a yield of 70%. Samples for analysis were obtained by short-path distillation of this product [160°–180° C. (bath temperature)/0.01 mmHg].

IR (neat): 1590, 1580, 1490, 1480, 1430, 1255, 1215, 840, 760, 690 cm$^{-1}$.

NMR (CDCl$_3$): $\delta$2.11s(3H), 2.40s(3H), 6.8–7.4m(9H).

Elemental analysis for C$_{16}$H$_{15}$ClOS$_2$: Calculated: C,59.52; H,4.68; S,19.86. Found: C,59.43; H,4.50; S,19.91.

EXAMPLE 26

Anhydrous methanol (15 ml) was added to 2.781 g (8.61 millimoles) of 1,1-bis(methylthio)-2-chloro-2-(m-phenoxyphenyl)ethylene, and 0.3 ml of methanol saturated with hydrogen chloride was added. The mixture was heated under reflux for 4 hours. The solvent was removed under reduced pressure, and the residue was chromatographed on a silica gel column using hexane/benzene as an eluant to afford 2.284 g of methyl α-methylthio(m-phenoxyphenyl) acetate as an oil in a yield 92%. Samples for analysis were obtained by simple distillation of this product [140°–160° C. (bath temperature)/0.02 mmHg].

IR (neat): 1740, 1585, 1490, 1250, 1150, 760, 690 cm$^{-1}$

NMR (CDCl$_3$): $\delta$2.04s(3H), 3.68s(3H), 4,42s(1H), 6.8–7.4m(9H).

Elemental analysis for C$_{16}$H$_{16}$O$_3$S: Calculated: C,66.64; H,5.59; S,11.12. Found: C,66.45; H,5.47; S,10.88.

EXAMPLE 27

Method A

1-Methylsulfinyl-1-methylthio-2-(p-dimethylaminophenyl)ethylene (1.500 g) was dissolved in 30 ml of chloroform, and 1.5 ml of triethylamine was added. With stirring at −20° C., 0.7 ml of thionyl chloride was added dropwise over the course of 5 minutes. The mixture was stirred at this temperature for 1 hour, and then at room temperature for 2 hours. Water (50 ml) was added. The organic layer was separated, and dried over anhydrous sodium sulfate. The dried product was concentrated under reduced pressure, and 20 ml of methanol and 1 ml of methanol saturated with hydrogen chloride were added. The mixture was heated under reflux for 14.5 hours, and concentrated under reduced pressure. A saturated aqueous solution of sodium bicarbonate was added, and the mixture was stirred for a while and then extracted three times with 50 ml of diethyl ether.

The organic layer was dried with anhydrous sodium sulfate, concentrated under reduced pressure, and chromatographed on a silica gel column using methylene chloride as an eluant to afford 713 mg of methyl α-methylthio(p-dimethylaminophenyl)acetate as pale yellow crystals in a yield of 51%.

Method B

A 1,1 N methanol solution (50 ml) of hydrogen chloride was added to 3.547 g of 1-methylsulfinyl-1-methylthio-2-(p-dimethylaminophenyl)ethylene, and the mixture was heated under reflux for 13 hours. The mixture was concentrated under reduced pressure, and a saturated aqueous solution of sodium bicarbonate was added to the residue until there was no foaming. The solid precipitated was collected by filtration, washed with a saturated aqueous solution of sodium bicarbonate, and water, and then dried in vacuo. Recrystallization of the resulting solid from hexane afforded 2.697 g of methyl α-methylthio(p-dimethylaminophenyl)acetate as colorless crystals in a yield of 81%.

Melting point: 80.5°–81.5° C.

IR (nujol): 1730 cm$^{-1}$

NMR (CDCl$_3$): $\delta$2.02s(3H), 2.89s(6H), 3.66s(3H). 4.40s(1H), 6.62d(2H, J=9 Hz), 7.25d (2H, J=9 Hz)

Elemental analysis for C$_{12}$H$_{17}$NO$_2$S: Calculated: C,60.22; H,7.16; N,5.85; S,13.40. Found: C,60.13; H,7.00; N,5.68; S,13.35.

EXAMPLE 28

Methyl α-methylthio(p-dimethylaminophenyl)acetate (1.215 g) was dissolved in 20 ml of methanol, and 30 ml of a 10% aqueous solution of sodium hydroxide was added. The mixture was stirred at 70° C. for 14 hours. The mixture was acidified to a pH of 5 with conc. hydrochloric acid, and continuously extracted with ethyl acetate. The organic layer was dried over anhydrous sodium sulfate, and the solvent was removed under reduced pressure to afford 0.951 g of α-methylthio(p-dimethylaminophenyl)acetic acid in a yield of 83%.

Melting point: 98.0°–99.0° C. (from diethyl ether)

IR (nujol): 3000–2500, 1730, 1690 cm$^{-1}$

NMR (CDCl$_3$): $\delta$2.06s(3H), 2.89s(6H), 4.30s(1H), 6.65d(2H, J=9 Hz), 7.26d(2H, J=9 Hz), 7.5 broad s(1H).

Elemental analysis for C$_{11}$H$_{15}$NO$_2$S: Calculated: C, 58.64; H, 6.71; N, 6.22; S, 14.23. Found: C, 58.67; H, 6.72; N, 6.13; S, 14.09.

EXAMPLE 29

Methyl α-methylthio(p-dimethylaminophenyl)acetate (105 mg) was dissolved in 10 ml of methanol, and 8.2 mg of sodium tungstate dihydrate and 0.6 ml of a 30% aqueous solution of hydrogen peroxide were added. The mixture was stirred at room temperature for 60 hours. The remaining hydrogen peroxide was decomposed with sodium thiosulfate, and 20 ml of water was added to the mixture. It was then extracted three times with 10 ml of methylene chloride. The organic layer was dried over anhydrous sodium sulfate, and concentrated under reduced pressure. Recrystallization of the residue from methanol afforded 76 mg of methyl α-methylsulfonyl(p-dimethylaminophenyl)acetate in a yield of 63.5%.

Melting point: 136.0°–136.5° C. (from hexane)

IR (nujol): 1735 cm$^{-1}$

NMR (CDCl$_3$): $\delta$2.84s(3H), 2.93s(6H), 3.78s(3H), 4.82s(1H), 6.66d(2H, J=8.5 Hz), 7.35d(2H, J=8.5 Hz).

Elemental analysis for C$_{12}$H$_{17}$NO$_4$S: Calculated: C, 53.12; H, 6.32; N, 5.16. Found: C, 52.96; H, 6.24; N, 4.96.

EXAMPLE 30

1-Methylsulfinyl-1-methylthio-2-(p-aminophenyl)-ethylene (892 mg) was dissolved in 90 ml of methanol, and 10 ml of methanol saturated with hydrogen chloride was added. The mixture was heated under reflux for 18 hours. The reaction mixture was concentrated under reduced pressure, and 60 ml of a saturated aqueous solution of sodium bicarbonate was added to the residue. The mixture was then extracted three times with 20 ml of methylene chloride. The organic layer was dried over anhydrous sodiu, sulfate, and concentrated under reduced pressure to afford 786 mg of methyl α-methylthio(p-aminophenyl)acetate as a pale yellow oil in a yield of 95%.

Boiling point: 157°–159° C./1.0 mmHg

IR (neat): 3500–3200, 1730 cm$^{-1}$

NMR (CDCl$_3$): δ2.04s(3H), 3.38 broad (2H), 3.72s(3H), 4.41s(1H), 6.67d(2H, J=8.5 Hz), 7.23d (2H, J=8.5 Hz).

Elemental analysis for C$_{10}$H$_{13}$NO$_2$S: Calculated: C, 56.85; H, 6.20; N, 6.63; S, 15.17. Found: C, 56.90; H, 6.17; N, 6.69; S, 14.94.

EXAMPLE 31

1-Methylsulfinyl-1-methylthio-2-(p-aminophenyl)-ethylene (47 mg) was dissolved in 2.0 ml of ethanol and 0.4 ml of conc. hydrochloric acid (about 11 N) was added. The mixture was heated under reflux for 7 hours. The reaction mixture was concentrated under reduced pressure, and a saturated aqueous solution of sodium bicarbonate was added to the residue. The mixture was extracted with methylene chloride. The organic layer was dried over anhydrous sodium sulfate, and concentrated under reduced pressure. The residue was separated, and purified by thin-layer chromatography (silica gel, benzene) to afford 41 mg of ethyl α-methylthio(p-aminophenyl)acetate as a pale yellow oil in a yield of 88%.

IR (neat): 3370, 1727, 1620, 1515, 1290, 1150 cm$^{-1}$

NMR (CDCl$_3$): δ2.02s(3H), 1.22t(3H, J=7.5 Hz), 4.14q(2H, J=7.5 Hz), 4.35s(1H), 6.58d(2H, J=8.5 Hz), 7.21d(2H, J=8.5 Hz), 3.65 broad (2H)

Mass spectrum: m/e 225 (M+), 178 (base peak), 152, 136, 106.

EXAMPLE 32

Method A of Example 27 was repeated except that 1-methylsulfinyl-1-methylthio-2-[3-chloro-4-(piperidinyl-1)-phenyl]ethylene was used instead of 1-methylsulfinyl-1-methylthio-2-(p-dimethylaminophenyl)ethylene, thereby to obtain methyl α-methylthio[3-chloro-4-(piperidinyl-1)-phenyl]acetate as an oil.

Method B of Example 27 was employed to obtain methyl α-methylthio[3-chloro-4-(piperidinyl-1)phenyl]acetate as follows:

A 1.1 N methanol solution of hydrogen chloride was added to 64.1 mg of 1-methylsulfinyl-1-methyltuio-2-[3-chloro-4-(piperidinyl-1)phenyl]ethylene, and the mixture was heated under reflux for 30 hours. The reaction mixture was concentrated under reduced pressure, and a saturated aqueous solution of sodium bicarbonate was added. The mixture was extracted with methylene chloride. The organic layer was dried over anhydrous sodium sulfate, and concentrated under reduced pressure. The residue was separated, and purified by thin-layer chromatography (silica gel, hexane) to afford 32 mg of methyl α-methylthio[3-chloro-4-(piperidinyl-1)phenyl]acetate as an oil in a yield of 52%.

IR (neat): 2920, 1740, 1605, 1500 cm$^{-1}$.

NMR (CDCl$_3$): δ2.10s(3H), 1.5–2.0m(6H), 2.8–3.2m(4H), 3.76s(3H), 4.23s(1H), 6.9–7.5m(3H).

Mass spectrum: m/e (M+, 7%), 268 (35%), 267 (21%), 266 (base peak), 208 (11%).

EXAMPLE 33

1-Methylsulfinyl-1-methyltyio-2-(m-benzoylphenyl)-ethylene (4.48 g) was dissolved in 20 ml of methylene chloride, and 3 ml of pyridine was added. With stirring under ice cooling, 3 ml of a methylene chloride solution containing 1.86 g of thionyl chloride was added dropwise over the course of 5 minutes. Under ice cooling, the mixture was further stirred for 30 minutes. Methylene chloride (20 ml) was added, and the mixture was washed three times with 10 ml of water. The organic layer was dried over anhydrous sodium sulfate, and the solvent was distilled off under reduced pressure. The residue was chromatographed on a Florisil column using hexane/benzene as an eluant to afford 3.574 g of 1,1-bis(methylthio)-2-chloro-2-(m-benzoylphenyl)ethylene as colorless crystals in a yield of 75%.

Melting point: 94°–96° C. (from methanol).

IR (KBr): 1655, 1295, 1215, 760, 720, 650 cm$^{-1}$.

NMR (CDCl$_3$): δ2.14s(3H), 2.41s(3H), 7.3–7.9m(9H).

Elemental analysis for C$_{17}$H$_{15}$ClOS$_2$: Calculated: C, 60.97; H, 4.52; S, 19.15. Found: C, 60.88; H, 4.56; S, 19.27.

EXAMPLE 34

Anhydrous methanol (20 ml) was added to 3.429 g of 1,1-bis(methylthio)-2-chloro-2-(m-benzoylphenyl)ethylene, and 0.3 ml of methanol saturated with hydrogen chloride was added. The mixture was heated under reflux for 7 hours. The solvent was distilled off under reduced pressure, and the residue was chromatographed on a silica gel column using benzene/methylene chloride as an eluant to afford 2.474 g of methyl α-methylthio(m-benzoylphenyl)-acetate as an oil in a yield of 81%. Samples for analysis were obtained by short-path distillation of this product [160°–180° C. (bath temperature)/0.01 mnHg].

IR (neat): 1740, 1660, 1280, 1150, 710 cm$^{-1}$

NMR (CDCl$_3$): δ2.06s(3H), 3.70s(3H), 4.52s(1H), 7.3–7.9m(9H).

Elemental analysis for C$_{17}$H$_{16}$O$_3$S: Calculated: C, 67.97; H, 5.37; S, 10.68. Found: C, 67.84; H, 5.19; S, 10.50.

REFERENTIAL EXAMPLE 2

This is an example of synthesizing a novel cephalosporin, 7-[α-methylthio(thinyl-2)acetamido]-3-acetoxymethyl-3-caphem-4-carboxylic acid.

One millimole of α-methylthio(thienyl-2)acetic acid was dissolved in 10 ml of dry tetrahydrofuran, and to this solution was added 1.1 millimoles of triethylamine and 1.1 millimoles of pivalcyl chloride at −15° C. The mixture was stirred for 1 hour, and cooled to −40° C. with dry ice-acetone. A solution obtained by stirring 1 millimole of 7-ACA and a millimoles of hexamethyldisilazane in 5 ml of acetonitrile at 10° C. for 30 minutes was added to the cooled solution, and the resulting mixture was stirred at −40° to −30° C. for 90 minutes, and then at room temperature for 90 minutes. The reaction mixture was concentrated under reduced pressure. Ethyl acetate was added to the residue, and the mixture was washed with 1 N hydrochloric acid and then with a saturated aqueous solution of sodium chloride. The ethyl acetate layer was dried over anhydrous sodium sulfate, and concentrated under reduced pressure. The residue was solidified from petroleum ether to afford the final product.

TLC: Rf=0.50

MIC (minimal inhibitory concentration) against Sarcina lutea ATCC 9341: ≦0.2 mcg/ml IR (nujol): δ3250, 1760, 1730, 1640, 1595, 1525, 1220, 1030, 720 cm$^{-1}$ In the thin-layer chromatography, a silica gel plate (20 cm plate) was used as a carrier, and a solvent consisting of benzene/dioxane/acetic acid/n-butanol in a ratio of 60/25/12/4 was used.

REFERENTIAL EXAMPLE 3

Synthesis of Ibuprefen:

Step 1

Methyl α-methylthio(p-isobutylphenyl)acetate (471 mg) was dissolved in 5 ml of anhydrous dimethylformamide, and with stirring under ice cooling, 75 mg (65% content) of sodium hydride was added. Hydrogen evolved immediately. When the mixture was stirred for about 10 minutes, the generation of hydrogen subsided. Methyl iodide (0.25 ml) was added, and the mixture was stirred under ice cooling for 30 minutes, and then at room temperature for 40 minutes. Then, an aqueous solution of ammonium chloride (0.5 g/30 ml) was added, and the mixture was extracted three times with 20 ml of diethyl ether. The organic layer was washed twice with 10 ml of water, dried over anhydrous sodium sulfate, and concentrated under reduced pressure. The residue was chromatographed on a silica gel column using hexane/benzene as an eluant to afford 422 mg of methyl α-(p-isobutylphenyl)-α-(methylthio)propionate as a colorless oil in a yield of 85%.

Boiling point: 118°–120° C./0.1 mmHg

IR (neat): 1735, 1245, 1105 cm$^{-1}$

NMR (CDCl$_3$): δ0.88d(6H, J=6 Hz), 1.78s(3H), 1.97s(3H), 1.5–2.0m(1H), 2.45d(2H, J=7 Hz), 3.76s(3H), 7.0–7.5 A$_2$B$_2$q(4H).

Mass spectrum: n/e 266 (M+), 251, 219 (base peak), 207, 191, 159.

Step 2

Water (2 ml) and 4 ml of methanol were added to 420 mg of methyl α-(p-isobutylphenyl)-α-(methylthio)propionate. Then, 280 mg (85% content) of potassium hydroxide was added, and the mixture was stirred at 60° C. for 2.5 hours. The reaction mixture, initially heterogeneous, became uniform. Water (30 ml) was added, and the mixture was extracted with 10 ml of methylene chloride. The aqueous layer was acidified with conc. hydrochloric acid to a pH of 1, and extracted three times with 20 ml of diethyl ether. The organic layer was dried over anhydrous sodium sulfate, and concentrated under reduced pressure to remove the diethyl ether. Thus, 394 mg of crude α-(p-isobutylphenyl)-α-(methylthio)propionic acid was obtained as an oil in a yield of 99%. The oil soon crystallized, and recrystallization from water/methanol afforded colorless crystals having a melting point of 89° to 92° C.

IR (KBr): 3000–2500, 1695, 1295, 1275, 940 cm$^{-1}$.

NMR (CDCl$_3$): δ0.90d(6H, J=6 Hz), 1.5–2.0m(1H), 1.80s(3H), 2.02s(3H), 2.46d(2H, J=7 Hz), 7.0–7.5 A$_2$B$_2$Q(4H), 13.9s(1H).

Step 3

α-(p-Isobutylphenyl)-α-(methylthio)propionic acid (387 mg) was dissolved in 3 ml of acetic acid, and 200 mg of zinc powder was added. The mixture was heated under reflux for 2 hours. Furthermore, 200 mg of zinc powder was added, and the mixture was heated under reflux for 18 hours. The zinc powder which agglomerated was pulverized, and the mixture was again heated under reflux for 20 hours. Water (30 ml) and 20 ml of ether were added, and the insoluble matter was separated by filtration. Then, conc. hydrochloric acid was added to adjust the pH of the mixture to 1, and it was extracted four times with 20 ml of diethyl ether. The organic layer was washed with 10 ml of water, dried over anhydrous sodium sulfate, and concentrated under reduced pressure to remove the diethyl ether and acetic acid. Thus, 319 mg of α-(p-isobutylphenyl)propionic acid was obtained as an oil which crystallized soon. The yield of the crude product was 100%. Recrystallization from hexane afforded colorless crystals having a melting point of 74° to 76° C. The IR and NMR spectra of this product were identical with those of the authentic sample.

REFERENTIAL EXAMPLE 4

Synthesis of Fenoprofen:

Step 1

Methyl α-methylthio(m-phenoxyphenyl)acetate (1.963 g) was dissolved in anhydrous dimethylformamide, and under ice cooling, 280 mg (65% content) of sodium hydride was added. The mixture was stirred for 10 minutes. Then, 0.60 ml of methyl iodide was added, and the mixture was stirred under ice cooling for 5 minutes and then at room temperature for 30 minutes. After adding an aqueous solution of ammonium chloride (500 mg/40 ml), the reaction mixture was extracted three times with 20 ml of diethyl ether, and washed three times with 10 ml of water. The product was dried over anhydrous sodium sulfate, and concentrated under reduced pressure. The residue was chromatographed on a silica gel column using hexane/benzene as an eluant to afford 1.930 g of methyl α-methylthio-α-(m-phenoxyphenyl)propionate as an oil in a yield of 94%. Distillation of this substance gave a fraction boiling at 147°–149° C./0.8 mmHg.

IR (neat): 1735, 1585, 1490, 1240, 1110, 930, 760, 695 cm$^{-1}$

NMR (CDCl$_3$): δ1.74s(3H), 1.96s(3H), 3.60s(3H), 6.7–7.4m(9H).

Elemental analysis for C$_{17}$H$_{18}$O$_3$S: Calculated: C, 67.52; H, 6.00; S, 10.60. Found: C, 67.56; H, 5.88; S, 10.47.

Step 2

Methanol (4 ml) and 2 ml of water were added to 663 mg of methyl α-methylthio-α-(m-phenoxyphenyl)propionate, and then 300 mg of sodium hydroxide was added. The mixture was heated under reflux for 2 hours. The mixture was diluted with 30 ml of water, and extracted with 10 ml of diethyl ether. The aqueous layer was acidified with about 1 ml of conc. hydrochloric acid, and extracted three times with 20 ml of diethyl ether. The organic layer was washed with 10 ml of water, and dried over anhydrous sodium sulfate. Concentration under reduced pressure gave 628 mg of α-methylthio-α-(m-phenoxyphenyl)propionic acid as an oil in a yield of 99%. This product crystallized on standing at room temperature. Recrystallization from hexane/carbon tetrachloride afforded colorless crystals having a melting point of 87° to 88° C.

IR (KBr): 3100–2500, 1695, 1595, 1585, 1490, 1255, 950, 750, 705, 690 cm$^{-1}$

NMR (CDCl$_3$): δ1.78s(3H), 2.04s(3H), 6.8–7.4m(9H), 10.30 broad s(1H).

Elemental analysis for $C_{16}H_{16}O_3S$: Calculated: C, 66.64; H, 5.59; S, 11.12. Found: C, 66.39; H, 5.52; S, 11.04.

Step 3

Water (1.5 ml) and 1.5 ml of conc. hydrochloric acid were added to 432 mg of α-methylthio-α-(m-phenoxyphenyl)propionic acid, and then 300 mg of zinc powder was added. With stirring, the mixture was heated under reflux for 2.5 hours. Water (10 ml) and 30 ml of diethyl ether were added to the reaction mixture. The insoluble matter was separated by filtration. The filtrate was extracted three times with 80 ml of diethyl ether. The organic layer was washed with 10 ml of water, and dried over anhydrous sodium sulfate. The solvent was removed under reduced pressure to afford 364 mg of α-(m-phenoxyphenyl)propionic acid as an oil. The yield was 100%.

REFERENTIAL EXAMPLE 5

Synthesis of Indoprofen:

Methyl α-methylthio(p-aminophenyl)acetate (760 mg) and 533 mg of phthalic anhydride were dissolved in 8 ml of acetic acid, and the solution was heated under reflux for 4 hours. The reaction mixture was concentrated under reduced pressure, and 100 ml of an aqueous solution of sodium bicarbonate was added. The mixture was extracted once with 20 ml of methylene chloride, and then twice with 10 ml of methylene chloride each time. The organic layer was dried over anhydrous sodium sulfate, and concentrated under reduced pressure to afford 1.222 g of methyl α-methylthio(p-phthalimidophenyl)acetate as colorless crystals in a yield of 99.5%.

Melting point: 168°-169° C. (from methanol)
IR (KBr): 1785 (w), 1765 (w), 1740, 1715 cm$^{-1}$
NMR (CDCl$_3$): δ2.11s(3H), 3.76s(3H), 4.55s(1H), 7.48d(2H, J=8.5 Hz), 7.60d(2H, J=8.5 Hz), 7.74-8.00m(4H).
Elemental analysis for $C_{18}H_{15}NO_4S$: Calculated: C, 63.33; H, 4.43; N, 4.10. Found: C, 63.27; H, 4.50; N, 4.01.

Step 2

Methyl α-methylthio(p-phthalimidophenyl)acetate (978 mg) was dissolved in 10 ml of anhydrous dimethylformamide, and under ice cooling, 120 mg of sodium hydride (65% content) was added. The mixture was stirred for 10 minutes. Then, 0.25 ml of methyl iodide was gradually added. The temperature was adjusted to room temperature, and the mixture was stirred for 5 minutes. An aqueous solution of ammonium chloride (500 mg/30 ml) was added, and the mixture was extracted four times with 20 ml of methylene chloride. The organic layer was washed with 10 ml of water, dried over anhydrous sodium sulfate, and then concentrated under reduced pressure. The residue was washed with 20 ml of hexane to afford 788 mg of methyl α-methylthio-α-(p-phthalimidophenyl)propionate as colorless crystals in a yield of 77%.

Melting point: 142°-145° C. (from ethanol).
IR (KBr): 1790, 1770, 1735, 1720, 1510, 1390, 1250, 1105, 890, 725 cm$^{-1}$.
NMR (CDCl$_3$): δ1.79s(3H), 1.99s(3H), 3.74s(3H), 7.3-8.0m(8H).
Mass spectrum: m/e 355 (M+), 308 (base peak), 2.96, 280, 248.

Step 3

Methanol (1 ml) and 1 ml of water were added to 178 mg of methyl α-methylthio-α-(p-phthalimidophenyl)propionate, and then 80 mg of sodium hydroxide was added. The mixture was stirred at room temperature for 1 hour, and then at 50° to 60° C. for 30 minutes. Conc. hydrochloric acid was added to adjust the pH of the mixture to 1, whereupon colorless crystals precipitated. The crystals were collected by filtration, washed with 15 ml of water, and dried. The amount of the dried crystals obtained was 152 mg.

These crystals (130 mg), 300 mg of zinc powder and 20 mg of anhydrous copper sulfate were added to 1.5 ml of acetic acid and the resulting mixture was heated under reflux for 5 hours with stirring. After cooling, 30 ml of methylene chloride and 20 ml of water were added. The insoluble precipitate was separated by filtration. The filtrate was acidified to a pH of 1 with conc. hydrochloric acid, and extracted three times with 60 ml of methylene chloride. The organic layer was washed with 20 ml of water, and dried over anhydrous sodium sulfate. The solvent was distilled off under reduced pressure to afford 86 mg of α-[p-(1-oxo-2-isoindolinyl)phenyl]propionic acid in a yield of 78%.

What we claim is:

1. A process for preparing an α-(alkylthio)acetic acid derivative of the formula

(IIIa)

wherein R represents a thienyl, furyl or aryl group, and R$^1$ and R$^2$ represent an alkyl group, which comprises reacting an α-chloroketene mercaptal of the formula

(II)

wherein R and R$^1$ are as defined above, with an alcohol of the formula

R$^2$OH wherein R$^2$ is as defined above, in the presence of an acid catalyst.

2. The process of claim 1 wherein the reaction is carried out at a temperature of 0° C. to 150° C.

3. The process of claim 1 wherein the alcohol is used in an excessive amount as a solvent, and the reaction is carried out in it.

4. A process for preparing an α-(alkylthio)acetic acid derivtive of the formula

(IIIa)

wherein R represents a thienyl furyl or aryl group, and R$^1$ and R$^2$ represent an alkyl group, which comprises reacting a ketene mercaptal S-oxide of the formula

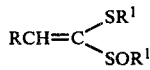
 (I)

wherein R and R¹ are as defined above, with an acid chloride to form an α-chloroketene mercaptal of the formula

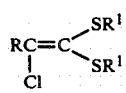
 (II)

wherein R and R¹ are as defined above, and reacting the α-chloroketene mercaptal with an alcohol of the formula $R^2OH$ wherein $R^2$ is as defined above, in the presence of an acid catalyst.

5. The process of claim 4 wherein the reaction of the ketene mercaptal S-oxide with the acid chloride is carried out at a temperature of −100° C. to room tmperature.

6. The process of claim 4 wherein the reaction of the ketene mercaptal S-oxide with the acid chloride is carried out in the presence of a base as an acid acceptor.

7. The process of claim 4 wherein the acid chloride is thionyl chloride or phsphorus oxychloride.

* * * * *